US00PP27242P3

(12) United States Plant Patent
Jones

(10) Patent No.: US PP27,242 P3
(45) Date of Patent: Oct. 4, 2016

(54) ***CALIBRACHOA* PLANT NAMED 'CCZRE07-0'**

(50) Latin Name: ***Calibrachoa* sp.**
Varietal Denomination: CCZRE07-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 121 days.

(21) Appl. No.: 14/544,296

(22) Filed: Dec. 20, 2014

(65) Prior Publication Data

US 2016/0183441 P1 Jun. 23, 2016

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — Anne Grunberg
(74) *Attorney, Agent, or Firm* — Cassandra Bright

(57) ABSTRACT

A new and distinct *Calibrachoa* cultivar named 'CCZRE07-0' is disclosed, characterized by large flower size and distinctive bright red flower color. Plants are characteristically dense and low mounding. The new variety is a *Calibrachoa*, normally produced as an ornamental outdoor garden or container plant.

2 Drawing Sheets

Latin name of the genus and species: *Calibrachoa* sp.
Variety denomination: 'CCZRE07-0'.

BACKGROUND OF THE INVENTION

The new *Calibrachoa* cultivar is a product of a planned breeding program conducted by the inventor, Steve Jones, in Santa Paula, Calif. The objective of the breeding program was to produce new *Calibrachoa* varieties for commercial ornamental applications. The cross resulting in this new variety was made during the Summer of 2011.

The seed parent is an unpatented, unnamed proprietary seedling variety of *Calibrachoa*, The pollen parent is an unpatented, unnamed proprietary seedling variety of *Calibrachoa*. The new variety was discovered in Spring of 2012 by the inventor in a group of seedlings resulting from the 2011 crossing, in a research greenhouse in Santa Paula, Calif.

Asexual reproduction of the new cultivar 'CCZRE07-0' by vegetative cuttings was first performed at a research greenhouse in Santa Paula, Calif. during the Summer of 2012. Subsequently, the new variety has been propagated by tissue culture and has shown that the unique features of this cultivar are stable and reproduced true to type in successive generations.

SUMMARY OF THE INVENTION

The cultivar 'CCZRE07-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CCZRE07-0' These characteristics in combination distinguish 'CCZRE07-0' as a new and distinct *Calibrachoa* cultivar:

1. Large flower size
2. Unique bright red flower color
3. Low growing, dense plant habit

PARENT COMPARISON

Plants of the new cultivar 'CCZRE07-0' were selected from bulk collected seed of proprietary seedlings. The exact seed and pollen parents are unknown.

COMMERCIAL COMPARISON

Plants of the new cultivar 'CCZRE07-0' are best compared to the variety *Calibrachoa* 'Spring Fling Red', unpatented in the United States. The two *Calibrachoa* varieties are similar in most horticultural characteristics, however, the new variety 'CCZRE07-0' differs in having an overall brighter red flower color and larger flower. Additionally, plants of the new variety produce more flowers per plant.

Plants of the new cultivar 'CCZRE07-0' can also be compared to the variety *Calibrachoa* 'Mini Famous Red', unpatented in the United States. The two *Calibrachoa* varieties are similar in most horticultural characteristics, however, the new variety 'CCZRE07-0' differs in having a larger flower. Additionally, plants of the new variety produce more flowers per plant.

BRIEF DESCRIPTION OF THE PHOTOGRAPHS

Figure 1:
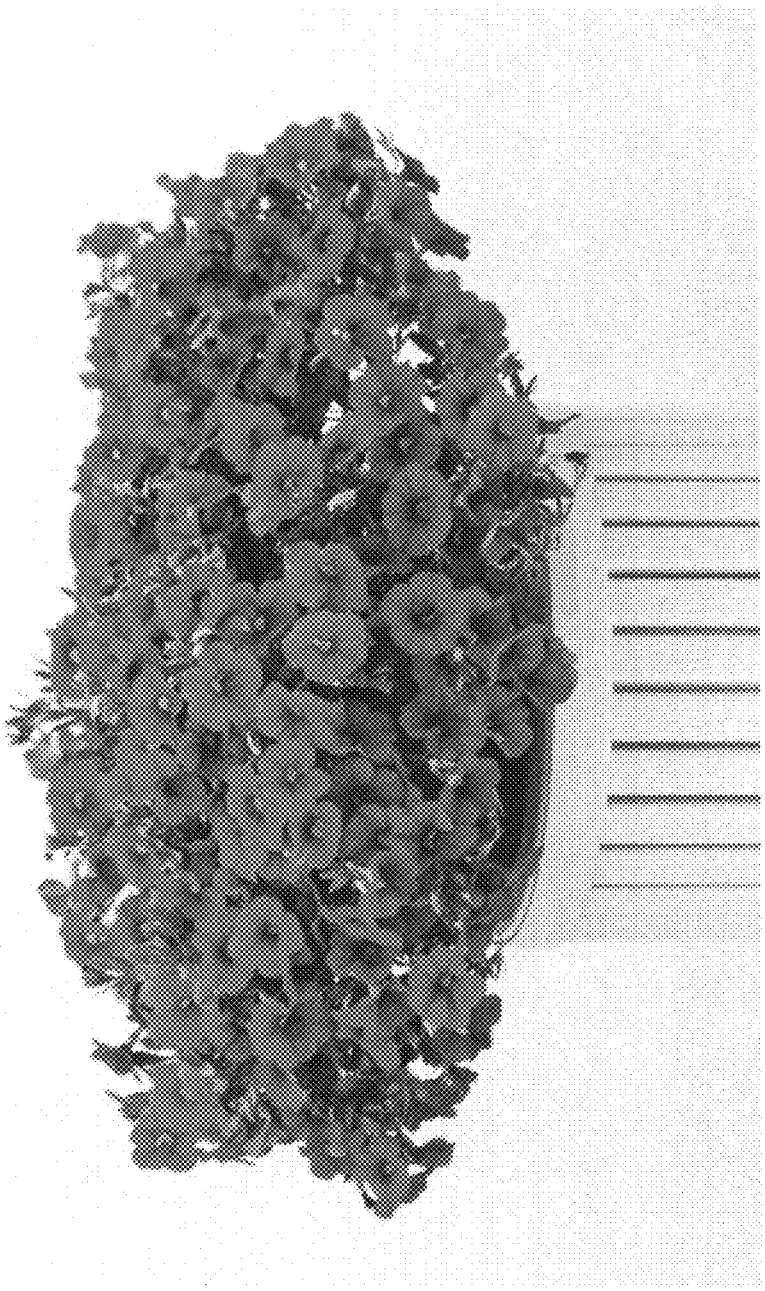

The accompanying photograph in FIG. 1 illustrates in full color a typical plant of 'CCZRE07-0' grown in a greenhouse, in a 10 inch pot.

Figure 2:
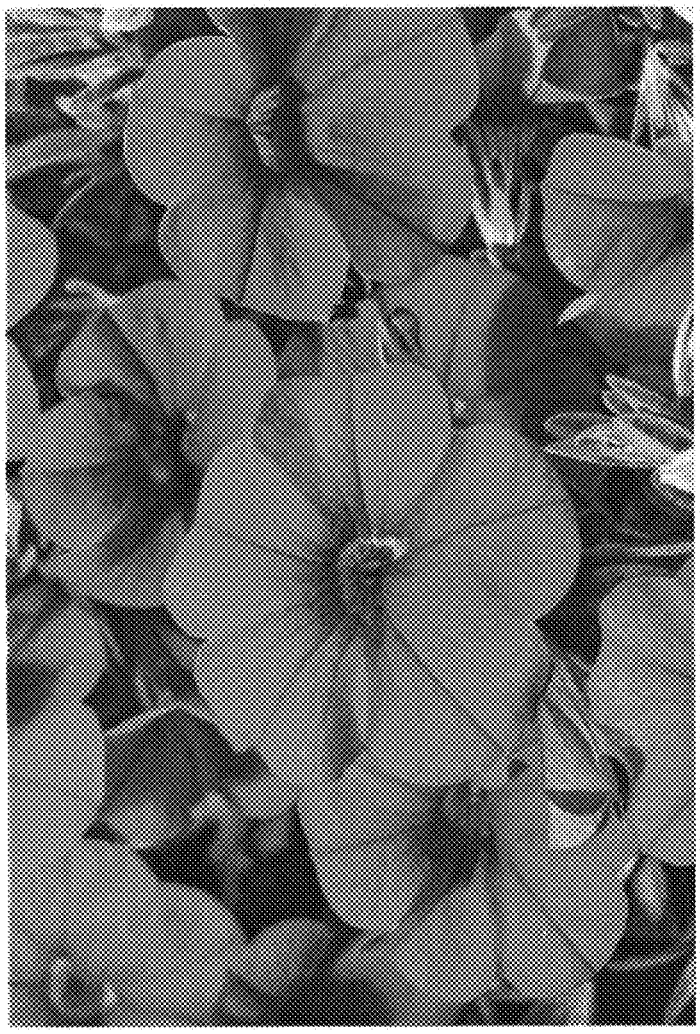

FIG. 2 illustrates in full color a close up of typical blooms. Age of the plant photographed is approximately 6 months from 5 rooted cuttings.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'CCZRE07-0' plants grown in a commercial greenhouse in Santa Paula, Calif. The growing temperature ranged from 18° C. to 25° C. The greenhouse is subject to partial shade. General light conditions are bright, normal sunlight with some shade during the brightest part of the day. Measurements and numerical values represent averages of typical plant types.

Botanical classification: *Calibrachoa* sp. 'CCZRE07-0'.

PROPAGATION

Time to initiate roots: About 10 to 12 days at approximately 25° C.

Root description: Fine, fibrous.

PLANT

Growth habit: Very low mounding.

Pot size of plant described: 10 inch.

Age of plant described: Approximately 6 months.

Height: Approximately 15 cm.

Plant spread: Approximately 45 cm.

Growth rate: Rapid.

Branching characteristics: Very free branching.

Length of primary lateral branches: Approximately 15 cm.

Diameter of lateral branches.: Approximately 0.3 cm.

Quantity of primary lateral branches: Approximately 24.

Characteristics of primary lateral branches:

- *Form*.—Round.
- *Color*.—Near RHS Green 143C.
- *Texture*.—Pubescent.
- *Strength*.—Strong.

Internode length: Average 0.5 to 1.5 cm.

FOLIAGE

Leaf:

- *Arrangement*.—Opposite.
- *Quantity*.—Average range near 12 to 20 per lateral branch.
- *Average length*.—Average 3.1 cm.
- *Average width*.—Average 1.1 cm.
- *Shape of blade*.—Oblanceolate.
- *Apex*.—Acute.
- *Base*.—Attenuate.
- *Margin*.—Entire.
- *Texture of surfaces*.—Highly pubescent both upper and lower surfaces.
- *Angle of attachment*.—75°.
- *Aspect*.—Flat.
- *Color*.—Young foliage upper side: Near RHS Green 138A. Young foliage under side: Near RHS Green 138B. Mature foliage upper side: Near RHS Green 137B. Mature foliage under side: Near RHS Green 137C.
- *Venation*.—Type: Pinnate. Venation color upper side: Near RHS Yellow-Green 144B. Venation color under side: Near RHS Yellow-Green 144B.
- *Petiole*.—Not Present.

FLOWER

Natural flowering season: All year round in moderate climates.

Days to flowering from rooted cutting: Approximately 4 weeks.

Inflorescence and flower type and habit: Terminal, Single, Salverform.

Rate of flower opening: 1 to 3 days from bud to fully opened flower.

Flower longevity on plant: About 4 to 7 days.

Approximate quantity of flowers per plant: 120 to 150 at 180 days old.

Persistent or self-cleaning: Self-cleaning.

Fragrance: Faint.

Bud:

- *Shape*.—Tubular.
- *Length*.—2.7 cm.
- *Diameter*.—0.7 cm.
- *Color*.—At proximal end Near RHS Yellow-Orange 17C, flushed and veins near Greyed-Purple 187A. At distal end Near RHS Red 53B.

Flower size:

- *Diameter*.—Average 4.5 cm.
- *Length*.—Average 3.9 cm.
- *Flower tube diameter at distal end*.—Average 1.3 cm.
- *Flower tube diameter at proximal end*.—0.5 cm.

Petals:

- *Length from throat*.—Average 2.2 cm.
- *Width*.—Average 2.2 cm.
- *Quantity*.—5 fused petals.
- *Texture*.—Smooth.
- *Apex*.—Broad acute.
- *Margin*.—Entire.
- *Color*.—When opening: Inner surface: Near RHS Red 53B. Outer surface: Near RHS Red 53D. Fully opened: Inner surface: Near RHS Red 46A. Outer surface: Near RHS Red 53B. Flower throat (inside): Near RHS Yellow-Orange 17A. Flower throat, vein: Near RHS Yellow-Green N144A. Flower tube (outside): Near RHS Red 53B. Flower tube, vein: Near RHS Yellow-Green N144A. Petal color, fading to: Near RHS Red 53B.

Calyx/sepals:

- *Quantity per flower*.—5.
- *Shape*.—Lanceolate.
- *Length*.—Approximately 1.5 cm.
- *Width*.—Approximately 0.4 cm.
- *Apex*.—Acute.
- *Base*.—Fused.
- *Margin*.—Entire.
- *Texture*.—Pubescent.
- *Color*.—Upper Surface: Near RHS Green 137A. Lower Surface: Near RHS Green 137B.

Peduncle:

- *Length*.—Average 1.8 to 3.0 cm.
- *Diameter*.—0.1 cm.
- *Texture*.—Pubescent.
- *Color*.—Near RHS Yellow-Green 144A.

*Orientation*.—Straight or slight undulation, 45° angle from stem.

REPRODUCTIVE ORGANS

Stamens:
*Number*.—5.
*Filament length*.—0.9 cm.
Anthers:
*Length*.—0.1 cm.
*Shape*.—Round.
*Color*.—Near RHS Yellow-Orange 17C.
*Pollen*.—Color: Near RHS Yellow-Orange 17A. Quantity: Scant.
Pistil:
*Number*.—1.
*Length*.—0.9 cm.
*Style*.—Length: 1 cm. Color: Near RHS Yellow 2B.
*Stigma*.—Shape: Bilobed. Color: Near RHS Yellow 2C. Ovary Color: Near RHS Yellow-Green 144C.

OTHER CHARACTERISTICS

Seeds and fruits: Not observed.
Disease/pest resistance: Neither resistance nor susceptibility to pathogens and pests common to *Calibrachoa* have been observed.
Temperature tolerance: The new variety tolerates temperatures between 3° C. to 40° C.

What is claimed is:

1. A new and distinct cultivar of *Calibrachoa* plant named 'CCZRE07-0' as herein illustrated and described.

* * * * *